United States Patent [19]

Overell

[11] 4,428,932

[45] Jan. 31, 1984

[54] PHARMACEUTICAL COMPOSITIONS

[75] Inventor: Brain G. Overell, North Holmwood, England

[73] Assignee: Beecham Group Limited, England

[21] Appl. No.: 373,290

[22] Filed: Apr. 29, 1982

[30] Foreign Application Priority Data

Apr. 29, 1981 [GB] United Kingdom ............... 8113209

[51] Int. Cl.$^3$ ............................................. A61K 39/36
[52] U.S. Cl. ........................................ 424/91; 424/88
[58] Field of Search ................................... 424/91, 88

[56] References Cited

U.S. PATENT DOCUMENTS 3,761,585 9/1973 Mullan et al. .......................... 424/91
4,258,029 3/1981 Moloney et al. ....................... 424/88

FOREIGN PATENT DOCUMENTS 18189 10/1980 European Pat. Off. .
4531159 3/1935 United Kingdom .

*Primary Examiner*—Esther M. Kepplinger
*Assistant Examiner*—Frederick W. Pepper
*Attorney, Agent, or Firm*—Jacobs & Jacobs

[57] ABSTRACT

A pharmaceutical composition, for use in the desensitization therapy of humans allergic to non-infective allergens, comprises a non-infective allergen and an adjuvant consisting of a $C_{10-22}$ alkyl ester of tyrosine or a pharmaceutically acceptable salt thereof.

8 Claims, No Drawings

PHARMACEUTICAL COMPOSITIONS

This invention relates to pharmaceutical compositions, their use in the therapy of allergic humans, and to a process for their preparation.

U.S. Pat. No. 4,258,029 discloses that esters of a long chain alcohol such as a $C_{10-22}$ alkanol and an amino acid can be used as adjuvants in antigenic compositions containing bacterial or viral antigens.

It has now surprisingly been found that such adjuvants are useful in non-infective allergen compositions, which compositions maybe used in the desensitisation therapy of humans allergic to non-infective allergens.

Accordingly, the present invention provides a pharmaceutical composition comprising a non-infective allergen and an adjuvant which comprises a $C_{10-22}$ alkyl ester of tyrosine or a pharmaceutically acceptable salt thereof.

The non-infective allergen for use in this invention is suitably in the form of an extract of whole allergen. By way of illustration pollens, such as grass pollens, for example rye; weeds, such as ragweed; house dust mites; dander; and Hymenoptera venoms, e.g. bee and wasp venoms are all suitable. These extracts of allergen are water soluble.

It will be appreciated that it is well known in the art that such allergens may be modified prior to use to achieve an optimisation of properties. By way of example, a glutaraldehyde modified allergen may be used, such materials being described fully in U.K. Pat. No. 1,282,163.

Other known formulation techniques may also be used with the allergens which are useful in this invention. They may for example be adsorbed (modified or unmodified) onto tyrosine, as fully described in U.K. Pat. Nos. 1,377,074 and 1,492,973.

Preferred alkyl esters for use in this invention are $C_{12-22}$ alkyl esters, particularly $C_{16-20}$ alkyl esters. The alkyl group is usually an n-alkyl group. Examples of suitable alkyl groups include n-decyl, n-dodecyl, n-tetradecyl, n-hexadecyl, n-octadecyl and n-eicosyl. The tyrosine may be in the D- or L-form, but is preferably in the L-form.

A particularly preferred composition of this invention comprises a non-infective inhalent allergen and n-octadecyl tyrosine, and a preferred non-infective allergen is a grass pollen, such as rye.

Suitable pharmaceutically acceptable salts of the tyrosine esters include acid addition salts with conventional acids such as hydrochloric, hydrobromic, phosphoric, sulphuric, citric, tartaric, lactic and acetic acids. A favoured salt is the hydrochloric salt.

The esters used in this invention may be formed by any convenient esterification process. By example, the alcohol and tyrosine may be heated together under reflux while hydrogen chloride gas is bubbled through the mixture, followed by conventional purification and isolation of the ester as its hydrochloride salt.

If desired, the salt may be basified and the resultant free ester extracted, purified and isolated. The free ester may be converted to another acid addition salt by treatment with the relevant acid.

The quantities of allergen used in the pharmaceutical compositions of the invention will be as conventional for that allergen in desensitisation therapy. By way of example the composition might suitably contain 0.1 to 10,000 pnu of allergen, the lower end of this range being more appropriate for early in the therapy, the higher end of this range being more appropriate for later in the therapy.

The quantities of tyrosine ester or salt thereof that can be used in the pharmaceutical compositions of this invention are to some extent dependent on the specific allergen and its dosage, but are usually within the conventionally used adjuvant quantity range. It is believed that it is a routine matter to derive a suitable level for the particular tyrosine ester or salt thereof and the particular allergen, to obtain the desired adjuvant effect coupled with pharmaceutical safety. By way of example, suitable levels of tyrosine ester or salt thereof might be in the range 0.1 to 10 more suitably 0.2 to 5, for example 1.0 mg per injection.

The pharmaceutical compositions of this invention may be used as vaccines in the desensitisation of allergic humans. Thus the compositions will suitably be in the form of solutions or suspensions, in a liquid vehicle. Preferably the compositions will be aqueous solutions or suspensions.

Usually a patient receiving treatment with such a composition is administered a number of injections, spread over a period of weeks or days.

The invention also provides a process for the preparation of the compositions of this invention, which process comprises bringing into conjunction the allergen and the tyrosine ester or salt thereof.

This process is conveniently carried out merely by adding the solid tyrosine ester or salt thereof to an aqueous solution of the allergen and stirring gently for some time, for example 24 hours. The resulting precipitation is then allowed to settle and the supernatant drawn off. The adsorbate, i.e. the precipitate which consists of allergen adsorbed onto tyrosine ester, may be resuspended and washed to remove excess allergen then suspended in a suitable solution, for example, phosphate buffered phenol saline ready for use.

Alternatively the adsorbate may be prepared by mixing a solution of the tyrosine ester, or a salt thereof, in a suitable organic solvent, for example, chloroform or diethyl ether, with an aqueous solution of the allergen. The proportions of each solvent are chosen such that the tyrosine ester, or salt thereof, precipitates upon mixing or alternatively the organic solvent is removed under vacuum thus causing precipitation of the tyrosine ester. The adsorbate thus formed is then processed as hereinbefore described.

It will, of course, be appreciated that the compositions of this invention may suitably contain as additional ingredients any of the conventional vaccine additives, such as sodium chloride, phosphates and preservatives.

The invention also provides a method of treating humans allergic to inhalent allergens, which method comprises administering to the sufferer an effective amount of a composition according to this invention.

The following Example illustrates the invention and the Description illustrates the preparation of an adjuvant.

DESCRIPTION

Preparation of octadecyl L-tyrosinate

A mixture of 1-octadecaol (13.3 g, 49.2 mmole) and L-tyrosine (6 g, 33.1 mmole) was heated at 120° for four hours. During this time the mixture was stirred vigorously and kept under a slow continuous stream of dry hydrogen chloride gas. The reaction was allowed to cool and then slurried with dichloromethane (100 ml). The slurry was filtered and the residue washed with more dichloromethane (2×50 ml). The residue was suspended in water and the pH adjusted to 8.0 with 1 M sodium hydroxide. The suspension was filtered and sucked dry. It was then extracted several times with diethyl ether (3×50 ml). The combined extracts were dried over MgSO$_4$ then filtered. The filtrate was treated with excess dry hydrogen chloride gas to precipitate octadecyl L-tyrosinate hydrochloride. The solid was filtered off, washed with ether and then partitioned between diethyl ether and dilute aqueous sodium hydroxide (pH 8). The aqueous solution was extracted with more ether and the combined extracts dried over MgSO$_4$ and concentrated at reduced pressure to give octadecyl tyrosinate, 1.53 g, 10.7% theoretical.

Mp. 80-3° C. $^1$H-nmr, CDCl$_3$ (TMS), , 0.86 (t, 3H,CH$_3$), 1.0–1.8 (m, 32H,—(CH$_2$)$_{16}$—), 2.98 (t,2H,—OCH$_2$), 3.5–3.9 (m,4H,OH,NH$_2$,CH), 4.17 (t, 2H,PhCH$_2$), 6.70 and 6.92 (2d,4H,Ph)—.

Microanalysis: C$_{27}$H$_{47}$NO$_3$ requires C 74.78; H 10.92; N 3.23. Found C 75.09; H 10.65; N 3.19.

EXAMPLE

Preparation of Injectable rye/octedecyl tyrosinate

A. Rye/tyrosine

Rye grass pollen extract (R.E.) (1 mg) was adsorbed to L-tyrosine (40 mg) in phosphate buffered phenol saline (1 ml).

The absorbate was prepared as follows:
Solution
 (1) 24% w/v L-tyrosine in 3.8 M. HCl;
 (2) 3.2 N. NaOH;
 (3) Na$_2$HPO$_4$ (11.8 g)+NaH$_2$PO$_4$.2H$_2$O (3.0 g) made up to 100 ml with water;
 (4) Phosphate buffered saline (Difco);
 (5) Phenol (5 g),
   NaCl (8 g),
   NaHPO$_4$ (0.2 g),
   NaH$_2$PO$_4$.2H$_2$O (1.5 g),
   made up to 1 liter with water and the pH adjusted to 7.0 with NaOH+HCl;
 (6) Rye grass pollen extract (R.E.) was made up at twice the final required concentration in 30 ml of solution (4).

10 ml of solution (3) was added to solution (6), then solution (1) (10 ml) and solution (2) (10 ml) were run into this at approximately 1 ml/minute using peristaltic pumps whilst stirring vigorously. The pH was not allowed to vary more than 0.5 pH units.

The resulting precipitate was centrifuged for 10 minutes and washed twice with solution (5) and resuspended with 60 ml of solution (5).

B. Rye/octadecyl tyrosinate 1

R.E. (1 mg) adsorbed to octadecyl tyrosinate (40 mg) in phosphate buffered saline (1 ml), was prepared by mixing an aqueous solution of R.E. with a solution of octadecyl tyrosinate in an organic solvent, and then removing the organic solvent under reduced pressure.

C. Rye/octadecyl tyrosinate 2

R.E. (1 mg) adsorbed to octadecyl tyrosinate (40 mg) in phosphate buffered saline (1 ml), was prepared by stirring solid octadecyl tyrosinate in an aqueous solution of R.E.

D. Rye/Freund's Complete Adjuvant

R.E. (1 mg) was prepared in an emulsion (1 ml) consisting of 2 parts phosphate buffered saline and 3 parts Freund's complete adjuvant (Difco).

PHARMACOLOGY

Immunisation Schedule

Four groups of six female mature Hartly strain guinea pigs received 1 ml sub-cutaneous injections of preparations A,B,C, or D respectively. The animals were bled on days 14 and 27 and sera prepared.

The sera were tested for the presence of R.E. specific haemagglutinating antibody by the standard method of "Chemical Modification of Crude Timothy Grass Pollen Extract Antigenicity and Immunogenicity changes following amino group modification—D. M. Moran and A. W. Wheeler, Int. Archs. Allergy. appl. Immunol. 50: 693–708 (1976)".

| Guinea pig Number | Immunogen Preparation | Haemagglutination Titre $-\log_2$ from ½ on day 14 | |
|---|---|---|---|
| | | 14 | 27 |
| A1 | A | <1 | <1 |
| A2 | | <1 | dead |
| A3 | | ND | <1 |
| A4 | | <1 | 4 |
| A5 | | 8 | 6 |
| A6 | | <1 | 3 |
| B1 | B | 6 | 8 |
| B2 | | 6 | 7 |
| B3 | | 4 | 7 |
| B4 | | 5 | 8 |
| B5 | | 7 | 8 |
| B6 | | 8 | 8 |
| C1 | C | 7 | 7 |
| C2 | | 7 | 6 |
| C3 | | <1 | 7 |
| C4 | | 3 | 7 |
| C5 | | 7 | 8 |
| C6 | | <1 | 7 |
| D1 | D | 6 | 11 |
| D2 | | 9 | 12 |
| D3 | | 8 | 13 |
| D4 | | <1 | 10 |
| D5 | | 2 | 11 |
| D6 | | 9 | 10 |

Conclusion

The effectiveness of octadecyl tyrosinate is shown in these tests. In these tests octadecyl tyrosinate is also shown to be a more effective adjuvant than tyrosine.

Toxicity

No toxic effects were observed in the above tests.

What is claimed is:

1. A pharmaceutical composition comprising a desensitizing effective amount of a non-infective allergen and an adjuvant effective amount of C$_{10-22}$ alkyl ester of tyrosine or a pharmaceutically acceptable salt thereof.

2. A composition according to claim 1, in which the alkyl ester is the n-decyl, n-dodecyl, n-tetradecyl, n-hexadecyl, n-octadecyl or n-eicosyl ester of tyrosine.

3. A composition according to claim 1, in which the non-infective allergen is selected from pollens, weeds, house dust mites, dander and Hymeroptera venoms.

4. A composition according to claim 1, comprising a non-infective allergen and n-octadecyl tyrosine.

5. A composition according to claim 1, in which the allergen is rye grass pollen.

6. A composition according to claim 1, in the form of a desensitisation vaccine for allergic humans.

7. A process for the preparation of a composition according to claim 1, which comprises bringing into conjunction the allergen and the tyrosine ester or salt thereof.

8. A method of treating allergy, which comprises administering to the sufferer an amount effective for desensitisation to non-infective allergen of a composition according to claim 1.

* * * * *